United States Patent
Martel et al.

(10) Patent No.: US 8,999,260 B2
(45) Date of Patent: Apr. 7, 2015

(54) STERILIZATION BOX SEAL DEVICE

(75) Inventors: Paul Martel, Vallauris (FR); Philippe Karacha, Roquefort-les-Pins (FR)

(73) Assignee: Sterlab, Vallauris (FR)

( * ) Notice: Subject to any disclaimer, the term of this patent is extended or adjusted under 35 U.S.C. 154(b) by 90 days.

(21) Appl. No.: 13/081,553

(22) Filed: Apr. 7, 2011

(65) Prior Publication Data
US 2011/0250104 A1  Oct. 13, 2011

(30) Foreign Application Priority Data
Apr. 9, 2010  (FR) .................................... 10 52701

(51) Int. Cl.
G09F 3/00  (2006.01)
A61L 2/00  (2006.01)
A61L 2/26  (2006.01)
A61B 19/02  (2006.01)
G09F 3/02  (2006.01)

(52) U.S. Cl.
CPC ........... *A61L 2/26* (2013.01); *G09F 2003/0207* (2013.01); *G09F 2003/0216* (2013.01); *A61B 19/02* (2013.01); *A61B 2019/0213* (2013.01); *A61L 2202/121* (2013.01); *A61L 2202/182* (2013.01)

(58) Field of Classification Search
CPC ................. B65D 55/02; G09F 2003/0216
USPC ................. 292/307 A, 307 B, 315–321, 325; 422/300
See application file for complete search history.

(56) References Cited

U.S. PATENT DOCUMENTS

| | | | | | |
|---|---|---|---|---|---|
| 1,937,743 | A | * | 12/1933 | Brooks | 292/328 |
| 4,149,329 | A | * | 4/1979 | Graves | 40/668 |
| 4,319,776 | A | | 3/1982 | Moberg | |
| 5,522,627 | A | | 6/1996 | Swift | |
| 5,535,491 | A | * | 7/1996 | Allport | 24/429 |
| 5,560,657 | A | * | 10/1996 | Morgan | 283/80 |
| 5,765,885 | A | * | 6/1998 | Netto | 292/318 |
| 2008/0236001 | A1 | | 10/2008 | Huenefeld | |

FOREIGN PATENT DOCUMENTS

EP  0786753 A2  7/1997

* cited by examiner

*Primary Examiner* — Kevin Joyner
*Assistant Examiner* — Liban Hassan
(74) *Attorney, Agent, or Firm* — Harness, Dickey & Pierce, PLC

(57) ABSTRACT

A sterilization box seal device including a shaft capable of being slid into a closure device of a sterilization box, and a support part of the proximal end of shaft, which includes a locking element irreversibly capable of cooperating and attaching on the distal end of shaft so as to form therewith a closed loop preventing the closure device from opening, such that the support part includes an additional part to the support one necessary for the sole seal function, the additional part includes an area capable of receiving a readable identification label.

6 Claims, 3 Drawing Sheets

STERILIZATION BOX SEAL DEVICE

FIELD

The invention relates to a seal device for equipments sterilization box, such as, in particular, medical and hospital utensils, carried out in closed apparatuses such as pre-vacuum type autoclaves and using saturated dry steam as a sterilizing gas, wherein sterilization boxes containing said equipments to be sterilized are introduced.

BACKGROUND

To prevent the boxes from being opened, by removal of their lid after this sterilization, and as long as the equipments contained in boxes are not needed, there are seals that indicate whether or not they have been opened.

For this purpose, seals like those described inter alia in the patents' applications and U.S. Pat. No. 5,522,627, EP 0 786 753 and U.S. Pat. No. 4,319,779 normally comprise a shaft, capable of being slid into an eyelet closure device such as that of the sterilization box in this present invention, and an arm pivoting on a support part of the shaft proximal end, the distal end of which is irreversibly capable of cooperating and attaching to the shaft distal end so as to form, with said shaft and their common support mount, a closed loop preventing the closure device from opening.

Said seals are mainly constituted of plastic pieces, and the nesting of their arm and shaft ends does not allow the reopening of the closed loop so formed, unless a portion of this piece is manually broken.

Generally, two seals, one of which is described below, are used per sterilization box for securing the two closure systems located on the two opposite sides of the lid and the box.

On the other hand, each sterilization box is labeled before or after sterilization so as to ensure its identification as well as the nature of the equipments it contains, in storages and/or places of use.

For this purpose, a label, of a rather considerable surface area, is placed on the box wall, close to the closure system so as to make it easy to read when boxes are stacked, and is either self-adhesive or slid into a label-holder.

The main disadvantage of this identification method is that the label either has to be removed from the sterilization box after use and this operation is not only unpractical but also leaves behind sticky adhesive residue, and even label residue on the box wall, or may fall out of the label-holder and be easily removed, creating thus a risk of error.

The problem here is how to avoid this disadvantage, while keeping, during the stacking of such sterilization boxes on top of each other, the readability of the identification labels of each box, as well as the recovery of the label during or after the opening of the box.

A solution to this problem is a seal device comprising a shaft slidable into a sterilization box closure device and a support part of the shaft proximal end, said support part comprising a locking element capable of irreversibly cooperating and attaching to the shaft distal end to form therewith a closed loop preventing the opening of the closure device, and according to the invention the shaft support part comprises an additional part to the support one which is only necessary to the seal function, said additional part comprises an area, the facial dimensions of which are preferably greater than those of the only support part, and sufficient for receiving a readable identification label.

SUMMARY

In a favorable embodiment, said additional part is a planar tab, foldable on the shaft support part which it covers, by folding along a line forming hinge, thus offering a view of the area opposite to the one facing the support part, and capable of receiving the identification label; besides, the fold line can be severed, the label-holder additional part being thus capable of separating from the seal device.

The result is a new seal device for sterilization boxes that addresses the problem and resolves the main disadvantage of the current labeling modes, either because the label does not need to be any longer removed, the box's area remaining intact, or because it remains solidly connected to seal and hence to the box without any risk of being easily removed.

DRAWINGS

The annexed FIG. 1 to 3 and the description below illustrate two exemplary embodiments of such a seal device according to the invention, yet other embodiments are still possible within the scope of the present invention.

DETAILED DESCRIPTION

A sterilization box 10 normally comprises a box body 7 and a removable lid 6 capable of being held on the box 7 body by means of two closure devices located on opposite sides of each other and usually in the box's rectangular parallelepiped shape.

Figure 1:
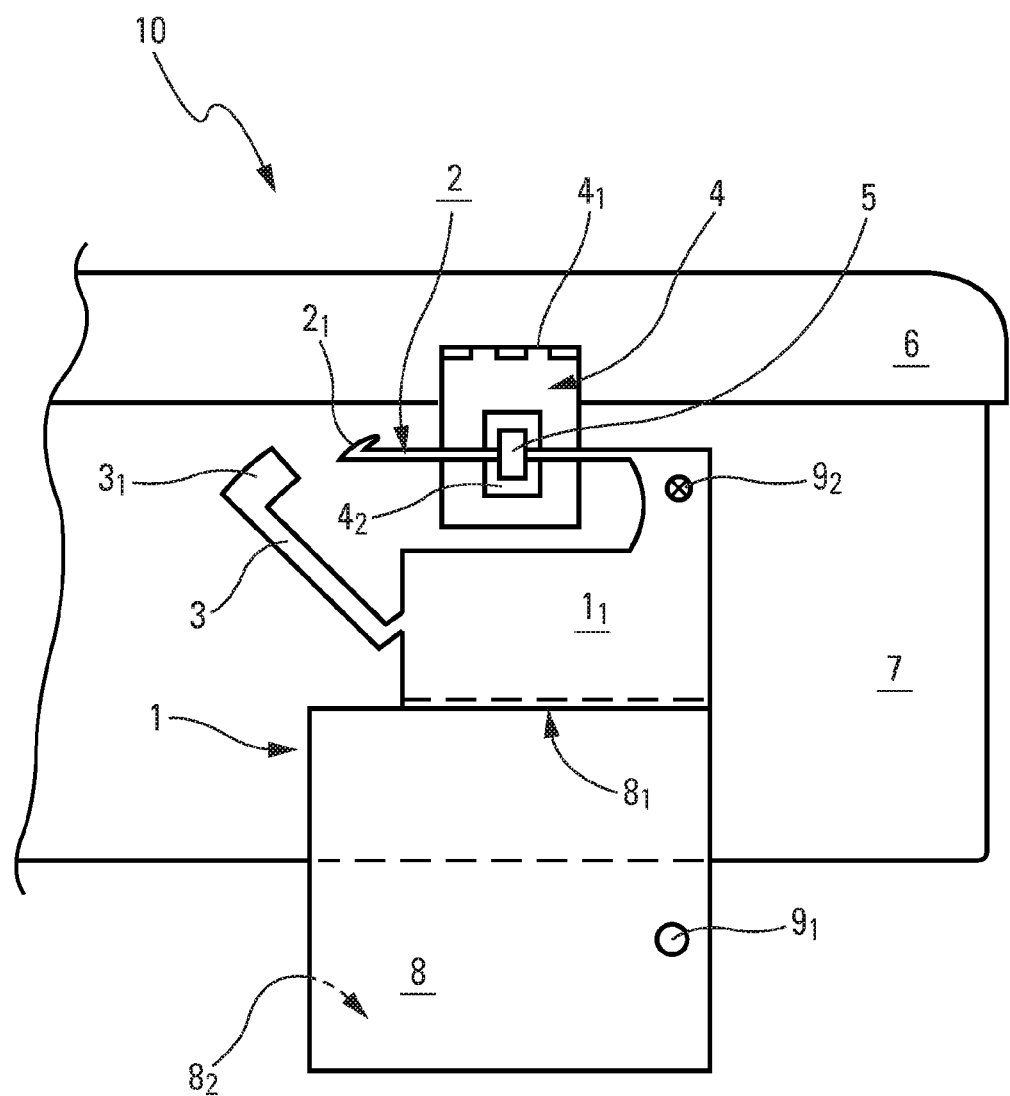
FIG. 1 is an overall view of a device according to the invention ready to be sealed on a sterilization box.

A closure device, as illustrated in FIG. 1, generally comprises an eyelet 5 capable of passing, in closed position, through a hinged tab hole $4_1$, said eyelet 5 and said tab 4 being one or the other solidly connected to the lid 6 whereas the other is solidly connected to the box 7 body. In another embodiment, a closure device made of two eyelets 5, may be available, one being solidly connected to the lid 6 and the other to the box 7 body and their orifices facing each other in lid 6 closing position on the box body 7.

The shaft 2 of the seal device is thus capable of passing through the closure device, that is to say through the orifice of said eyelet 5 (or of the two eyelets when the closure device comprises two eyelets, as stated above), and a support part $1_1$ of the shaft 2 proximal end comprises a locking element $3_1$ depicted here as the distal end of an arm 3 pivoting on a support part $1_1$, and which is irreversibly capable of cooperating and attaching to the shaft 2 distal end $2_1$, by nesting aforementioned shaft in a locking receptacle with a lug system preventing the unnesting, the whole forming a closed loop locking the tab 4 in the closed position.

The support part 1 comprises an additional part 8 to the support one $1_1$ essential for the only seal function: said support part $1_1$ often comprises a base having an area whereon can be affixed a reference, but of small dimension since its raison d'étre is, on the one hand, to reinforce the basis, and/or on the other hand, to ensure a better grip by the operator who often handles the seal device with one hand only. In addition, such a small area of the support part $1_1$, as illustrated in the annexed figures, does not allow to affix a full readable identification label 12: readability means that it is easy to write and read several references such as a code, date, intervening companies, and the nature or even the list of equipments contained in the sterilization box, which may stand in for 10 writing lines (as indicated by letters the height of which has to be favorably at least 5 mm so as to be precisely easily readable, and dashes in FIG. 3). Said additional part 8 of this invention comprises an area 8₂ capable of receiving such an identification label 12 which is normally 5 cm squared.

To this end, the face surface dimensions of this additional part 8, that is to say, in width and length such as those illustrated in the figures' plan, are favorably larger than those of the only support part 1₁ and sufficient to receive the readable identification 12 label: for this purpose, its width can be bigger than that of the support part 1₁ and its length or height making it possible for the label to run over the sterilization box 7 body bottom.

Besides, to allow the stacking of boxes, this label-holder additional part 8 is a planar tab in the shape of a plate foldable on the support part 1₁ of the shaft 2 and in the present exemplary embodiment of the arm 3 it covers, by folding along a line 8 forming hinge thus exposing area 8₂ opposite to the one facing the support part 1₁, and capable of receiving the identification label 12. Moreover, the additional part 8 folding like a "wallet" protects part 1₁, forming the seal it covers.

Figure 3:
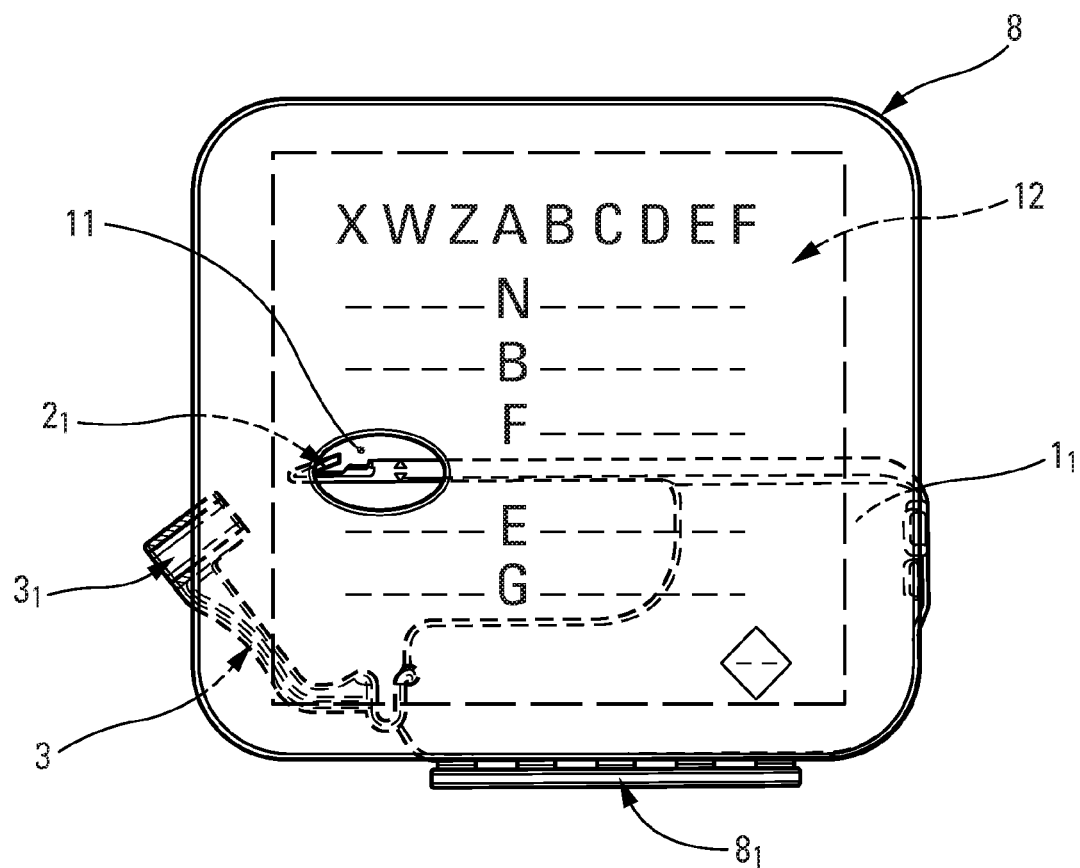
FIG. 3 is a view of the device of FIG. 2 in open position relating to the parts capable of sealing but with its additional part folded thereon.

To be able to control and check, once the additional part 8 is folded (and which does not bear a label contrary to what is shown in FIG. 3 because this one is often affixed at the end of the sterilization cycle) that the seal is well locked and remained locked during all operations, aforementioned additional part 8 comprises an aperture 11 that corresponds, when it is folded, to the place whereof the distal end 2₁ of the shaft 2 and the locking element 3₁ that can be at the end of the arm, mutually lock, as illustrated in FIG. 3, even if, in this figure, these ends are not illustrated as mutually locked: this hole 11 allows a direct visual control of the position of these one.

Figure 2:
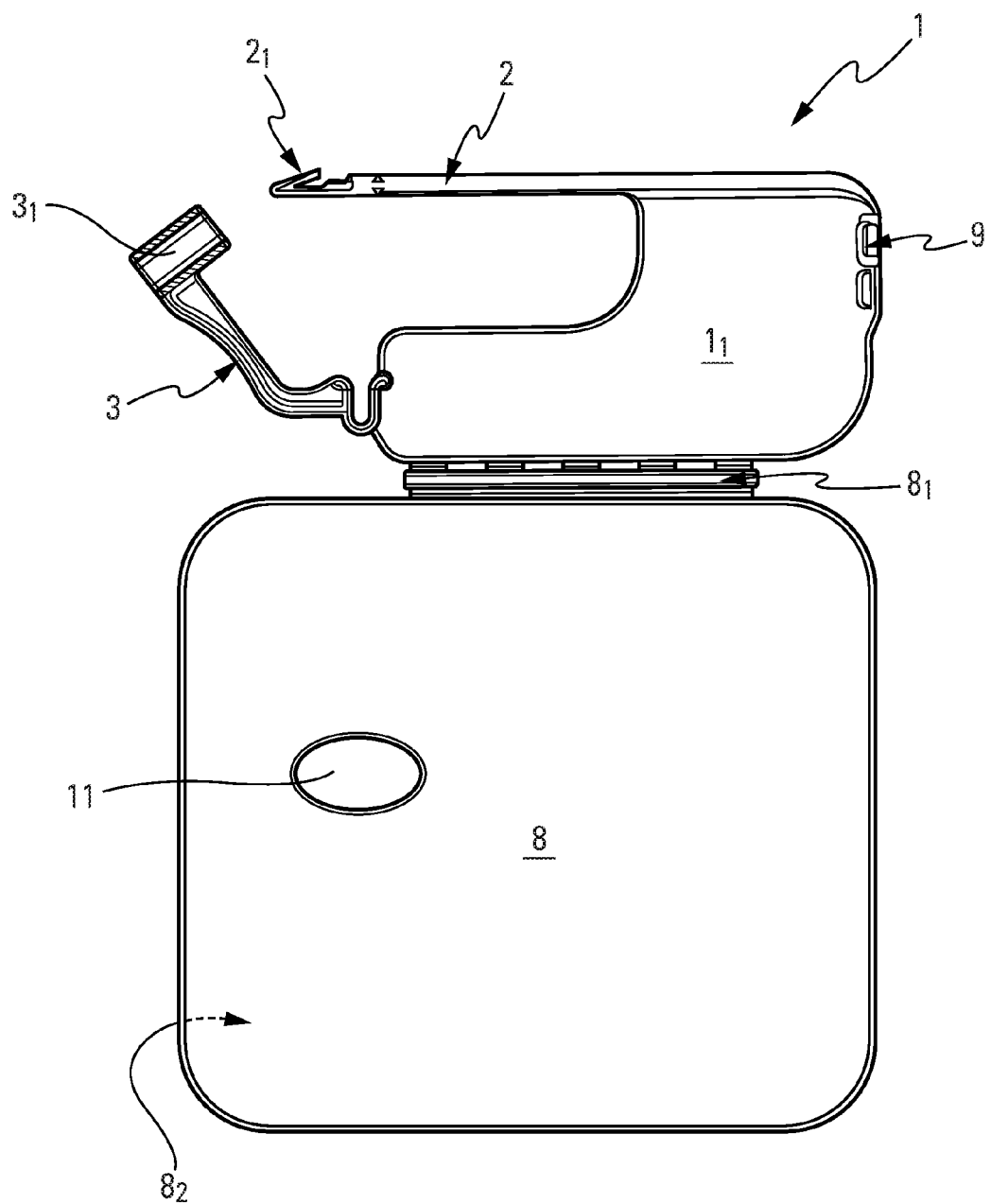
FIG. 2 is a view of the device according to the invention in open position as in FIG. 1 but illustrated without a sterilization box.

To hold this additional 8 part folded against the support part 1₁, these both support 1₁ and additional 8 parts comprise a holding device 9, such as by "clipping" or any device similar to a snap fastener, constituted of elements capable of cooperating with each other, either like in FIG. 1 with two elements 9, each one on each support 1₁ and additional 8 parts, either with one element 9, like in FIGS. 2 and 3, connected to one of the parts and in the form of deformable groove wherein is housed the edge of the other part.

According to FIG. 1, one of the elements solidly connected to the support part 1₁ can be a lug 9₂ projecting at the surface of this support part 1₁, and the other element 9₁ solidly connected to the foldable additional part can be a simple hole wherethrough lug 9₂ can pass and remain blocked.

Favorably, the holding element 9, or the "clipping" element allows a reversible holding or "clipping" (either in FIG. 1 by separation of lug 9₂ and hole 9₁, or in FIG. 2 and by lateral deformation of the groove 9 to release the edge of the additional part 8): this holding element 9 is thus capable of allowing spacing apart of the additional part 8 and the support part 1₁ by rotation along the line 8₁.

In addition, the fold hinge-forming line 8₁ is capable of being cut out, the label-holder additional part 8 being thus separated from the seal device so that the label is preserved without need to remove it from seal device.

The invention claimed is:

1. A sterilization box seal device comprising: a shaft, a support part, and a planar tab, the shaft being slidable into a closure device of a sterilization box, the support part being attached to a proximal end of the shaft, said support part comprising a locking element capable of irreversibly cooperating with and attaching to a distal end of the shaft to form therewith a closed loop preventing the closure device from opening, said locking element disposed at a distal end of an arm pivotably coupled to the support part, said planar tab being selectively detachable from said support part such that said planar tab is connected to said support part in a first condition and detached from said support part in a second condition, said planar tab receiving a readable identification label on an outer surface thereof, opposite the support part, and retaining said readable identification label thereon when said planar tab is in said first condition and when said planar tab is in said second condition, said planar tab foldable on the support part, such that said planar tab covers said support part by folding along a hinge-forming line and thus exposing the outer surface of said planar tab,
wherein said closed loop prevents the closure device from opening when said planar tab is in said first condition and when said planar tab is in said second condition such that said planar tab is not necessary for preventing the closure device from opening and, wherein the planar tab comprises an aperture corresponding, when folded, to the location where the shaft distal end and the locking element mutually lock.

2. The device according to claim 1, wherein the support part and planar tab include a holding device constituted of elements capable of cooperating with one another for holding the planar tab folded against the support part.

3. The device according to claim 2, wherein the holding device comprises two holding elements each one on each of the support part and the planar tab, separable and capable of allowing the spacing of the planar tab from the support part through rotation along the hinge-forming line.

4. The device according to claim 3, wherein the hinge-forming line is capable of being cut out, the planar tab being thus capable of being separated from the seal device.

5. The device according to claim 1, wherein the hinge-forming line is capable of being cut out, the planar tab being thus capable of being separated from the sterilization box seal device.

6. The device according to claim 1, wherein each of the support part and the additional part has a surface area, wherein the surface area of the planar tab is greater than the surface area of the support part.

* * * * *